US012257049B2

United States Patent
Rehan et al.

(10) Patent No.: US 12,257,049 B2
(45) Date of Patent: *Mar. 25, 2025

(54) INTEGRATED FIBER OPTIC SENSOR UMBILICAL CATHETER

(71) Applicants: Los Angeles BioMedical Research Institute at Harbor UCLA Medical Center, Torrance, CA (US); Intelligent Optical Systems, Torrance, CA (US)

(72) Inventors: Virender Rehan, Torrance, CA (US); Jesus Delgado, Torrance, CA (US)

(73) Assignees: Los Angeles BioMedical Research Institute at Harbor UCLA Medical Center, Torrance, CA (US); Intelligent Optical Systems, Torrance, CA (US)

(*) Notice: Subject to any disclaimer, the term of this patent is extended or adjusted under 35 U.S.C. 154(b) by 208 days.

This patent is subject to a terminal disclaimer.

(21) Appl. No.: 17/839,212

(22) Filed: Jun. 13, 2022

(65) Prior Publication Data

US 2022/0313127 A1 Oct. 6, 2022

Related U.S. Application Data

(63) Continuation of application No. 16/321,798, filed as application No. PCT/US2017/044219 on Jul. 27, 2017, now Pat. No. 11,389,095.

(Continued)

(51) Int. Cl.
| | |
|---|---|
| *A61B 5/1455* | (2006.01) |
| *A61B 5/00* | (2006.01) |
| *A61B 5/01* | (2006.01) |
| *A61B 5/1459* | (2006.01) |
| *A61B 5/145* | (2006.01) |
| *A61B 5/15* | (2006.01) |

(52) U.S. Cl.
CPC .......... *A61B 5/14557* (2013.01); *A61B 5/01* (2013.01); *A61B 5/14552* (2013.01);
(Continued)

(58) Field of Classification Search
CPC .............. A61B 5/1455; A61B 5/14551; A61B 5/14552; A61B 5/14556; A61B 5/14557;
(Continued)

(56) References Cited

U.S. PATENT DOCUMENTS

| | | | |
|---|---|---|---|
| 3,847,483 A | 11/1974 | Shaw et al. | |
| 4,861,727 A * | 8/1989 | Hauenstein | A61B 5/1459 |
| | | | 252/301.36 |

(Continued)

FOREIGN PATENT DOCUMENTS

| | | |
|---|---|---|
| EP | 0 283 289 A2 | 9/1988 |
| WO | WO-2004/026127 A1 | 4/2004 |

OTHER PUBLICATIONS

Extended European Search Report dated Jan. 8, 2020, from application No. 17835289.4.
(Continued)

*Primary Examiner* — Chu Chuan Liu
(74) *Attorney, Agent, or Firm* — Foley & Lardner LLP

(57) ABSTRACT

Embodiments described herein relate to a catheter configured to detect at least one blood gas parameter present in blood in an artery of a patient, including, but not limited to, a catheter wall forming at least one lumen configured for umbilical arterial catheterization, at least one optical fiber incorporated in the catheter wall, wherein the at least one optical fiber is configured to detected the at least one blood gas parameter.

19 Claims, 6 Drawing Sheets

Related U.S. Application Data

(60) Provisional application No. 62/368,951, filed on Jul. 29, 2016.

(52) U.S. Cl.
CPC .......... *A61B 5/1459* (2013.01); *A61B 5/6852* (2013.01); *A61B 5/14539* (2013.01); *A61B 5/150038* (2013.01); *A61B 5/4839* (2013.01); *A61B 2503/045* (2013.01); *A61B 2505/03* (2013.01); *A61B 2562/0233* (2013.01); *A61B 2562/0271* (2013.01)

(58) Field of Classification Search
CPC ... A61B 5/1459; A61B 5/6852; A61B 5/6876; A61B 5/01; A61B 5/14539; A61B 5/150038; A61B 5/002; A61B 5/4839; A61B 2562/0233; A61B 2562/043; A61B 2562/0271
See application file for complete search history.

(56) References Cited

U.S. PATENT DOCUMENTS

| | | | |
|---|---|---|---|
| 4,889,407 A * | 12/1989 | Markle | .............. G01N 21/7703 250/230 |
| 5,005,576 A | 4/1991 | Günther | |
| 5,284,138 A | 2/1994 | Kujawski | |
| 5,335,305 A | 8/1994 | Kosa et al. | |
| 5,596,988 A | 1/1997 | Markle et al. | |
| 5,928,155 A | 7/1999 | Eggers et al. | |
| 8,694,069 B1 | 4/2014 | Kosa et al. | |
| 2008/0188725 A1 | 8/2008 | Markle et al. | |

OTHER PUBLICATIONS

Jesus, et al., Integrated Fiber Optic Sensor Umbilical Catheter for Blood Gas Monitoring. Grant Abstract [online] (Intelligent Optical Systems) 2014 [retrieved on Sep. 27, 2017]. Retrieved from the Internet: <URL:http://grantome.com/grant/NIH/R43-HD080275-01A1>. abstract.

International Preliminary Report on Patentability dated Feb. 7, 2019, from application No. PCT/US2017/044219.

International Search Report and Written Opinion dated Dec. 15, 2017, from application No. PCT/US2017/044219.

Morgan, et al. "Continuous neonatal blood gas monitoring using a multiparameter intra-arterial sensor", Archives of Disease in Childhood Fetal and Neonatal Edition, vol. 80, No. 2, Mar. 1, 1999, pp. F93-F98.

US Non-Final Office Action dated Oct. 22, 2021, from U.S. Appl. No. 16/321,798.

US Notice of Allowance dated Mar. 7, 2022, from U.S. Appl. No. 16/321,798.

* cited by examiner

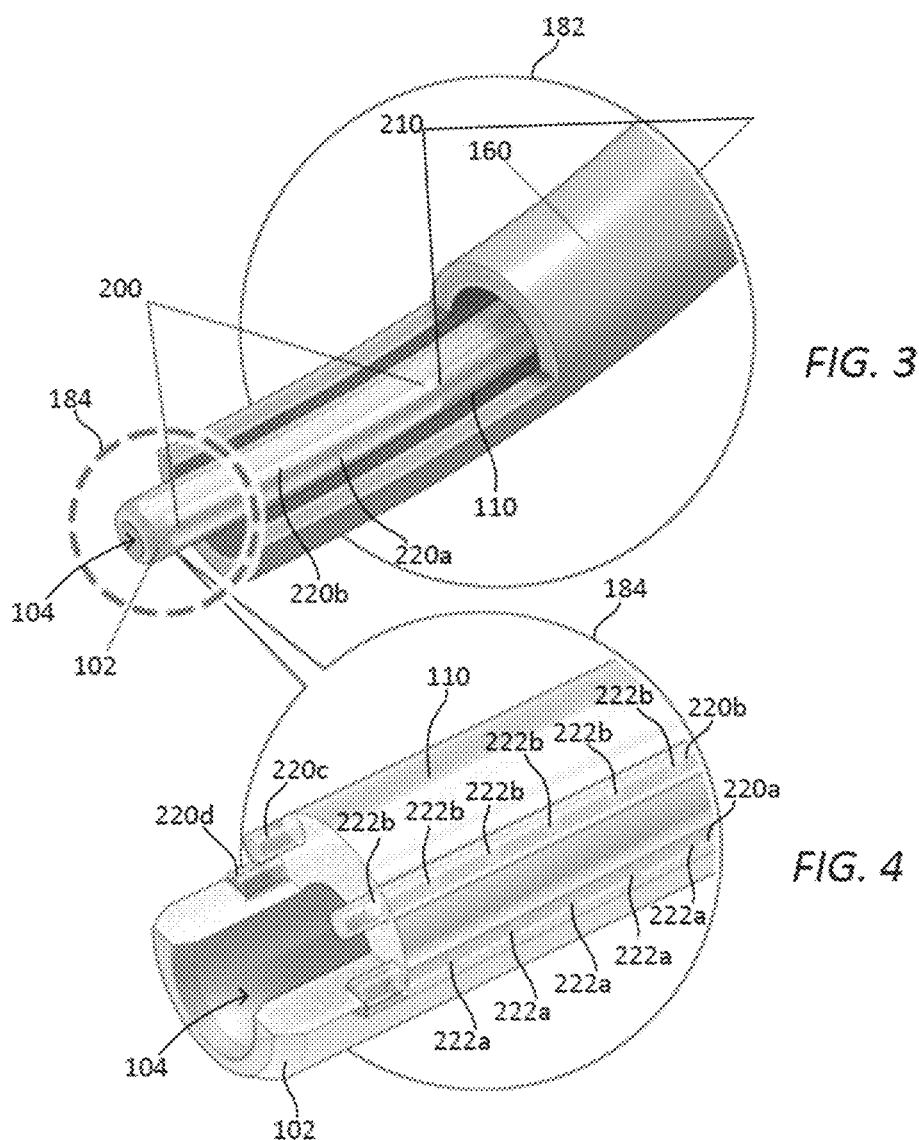

INTEGRATED FIBER OPTIC SENSOR UMBILICAL CATHETER

CROSS-REFERENCE TO RELATED PATENT APPLICATIONS

This application is a continuation of U.S. patent application Ser. No. 16/321,798, filed Jan. 29, 2019, which is a national stage entry of PCT Application No. PCT/US2017/044219, filed Jul. 27, 2017, which claims priority from U.S. Provisional Patent Application No. 62/368,951, filed Jul. 29, 2016, which relates to U.S. Provisional Patent Application No. 62/368,793 titled Distributed Fiber Optic Chemical Sensor and Method, filed on Jul. 29, 2016, which are incorporated herein by reference in their entirety.

GOVERNMENT RIGHTS

This invention was made with government support under 2R44HD80275-02A1 and 1R43HD080275-01A1 awarded by the National Institutes of Health. The government has certain rights in the invention.

BACKGROUND

In treatment and management of sick infants, accurate monitoring of arterial blood gases is essential, especially in the cases in which the infant is vulnerable and extremely premature given that even a minimal delay in appropriate interventions can be the difference between life and death. Conventional intensive care monitoring methods in neonatal intensive care unit are deficient in that they can merely provide intermittent (non-continuous) monitoring of blood gases, thus enabling only spot checking of physio-pathological status of the patient. Moreover, results following the traditional blood gas monitoring are usually delayed and distant from the actual triggering event that results in blood gas analysis. In addition, the conventional procedures involving blood draws are painful, predispose to iatrogenic infections, and can cause significant blood loss over time. Multiple blood transfusions are usually needed to replenish the resultant blood loss. Repeated and painful blood sampling experience can furthermore have long-term adverse developmental consequences.

Although continuous and non-invasive monitoring of blood gasses is preferred, current continuous and non-invasive modalities are significantly limited. Various attempts to develop continuous and non-invasive blood gas monitoring systems were unsuccessful, and no commercially available systems exist that meet accuracy, precision, and safety needs. Pulse oximetry, transcutaneous arterial $O_2$ and $CO_2$ tensions, continuous capnography, and/or the like have severe limitations. For example, most existing fiber optic sensors are point sensors on fiber tips that require controlled conditions at the sensing point to avoid errors. Point sensors in the radial artery of humans show frequent and unpredictable drops in Partial Pressure of Oxygen ($PaO_2$) due to the point fiber optic sensors intermittently contacting the arterial wall (instead of the bloodstream), resulting in measuring the tissue gas parameter values at the arterial wall instead of blood gas parameter values. This is called the "wall effect." As an alternative to intravascular sensing, extracorporeal in-line optical sensors are not practical in most instances, especially for neonates because it is a separate procedure with a whole range of issues associated with it, rendering it impractical under most circumstances.

Neonatal Intensive Care Units (NICUs) around the United States admit approximately 450,000 infants every year. Viewed in context of a domestic annual birth rate of nearly 4,000,000, the NICU admissions account for 11.25% of all births. Intravascular catheters are used for continuous blood pressure monitoring and arterial blood sampling and are considered "lifelines" for critically sick infants. The insertion of vascular catheters is the most commonly performed procedure in NICUs. Most critically ill newborns receiving at least one intravascular catheter, with umbilical arterial catheterization being the most common arterial catheterization procedure performed for such newborns. An umbilical arterial catheter is placed in a target patient to provide direct access to the central arteries.

SUMMARY OF THE INVENTION

Examples described herein related to an Integrated Fiber Optic Sensor Umbilical (ISUM) Catheter that is accurate, precise, and intrinsically safe, especially for neonates. For instance, the ISUM Catheter may combine routinely performed intravascular catheterization (such as, but not limited to, umbilical artery catheterization) with blood gas measuring elements to provide continuous and non-invasive blood gas monitoring. The ISUM Catheter may include one or more blood gas parameter sensors embedded in an umbilical catheter for continuously monitoring, in real time, blood gas parameters (e.g., $PaO_2$, $PaCO_2$, bicarbonate, pH, temperature, a combination thereof, and/or the like). The ISUM Catheter can be inserted into a body of a patient to access an artery (e.g., a central artery) in a manner consistent with intravascular catheterization (e.g., umbilical arterial catheterization). Accordingly, pain, iatrogenic infections, and blood loss can be reduced or eliminated.

In some examples, the ISUM Catheter as described herein may allow the gas sensors to sense in larger areas, thus reducing or eliminating probe placement or movement artifacts in data output. In some examples, the ISUM Catheter may have a dual-oxygen sensor and data fusion configuration associated with improved reliability. In some examples, placement of various gas or other types of sensors in an artery can eliminate the blood gas monitoring problems associated with vessel spasm. In some examples, the various gas or other types of sensors can be calibration-free, thus having no delay in data acquisition time. In some examples, the ISUM Catheter as described has a highly-repeatable configuration and can be produced in batches of hundreds, thereby reducing costs of the device.

BRIEF DESCRIPTION OF THE DRAWINGS

FIG. 3 is an enlarged perspective view of a catheter shown to be inserted into an artery in accordance with some embodiments.

FIG. 4 is an enlarged perspective view of a catheter in accordance with some embodiments.

DETAILED DESCRIPTION

Figures 1, 2:
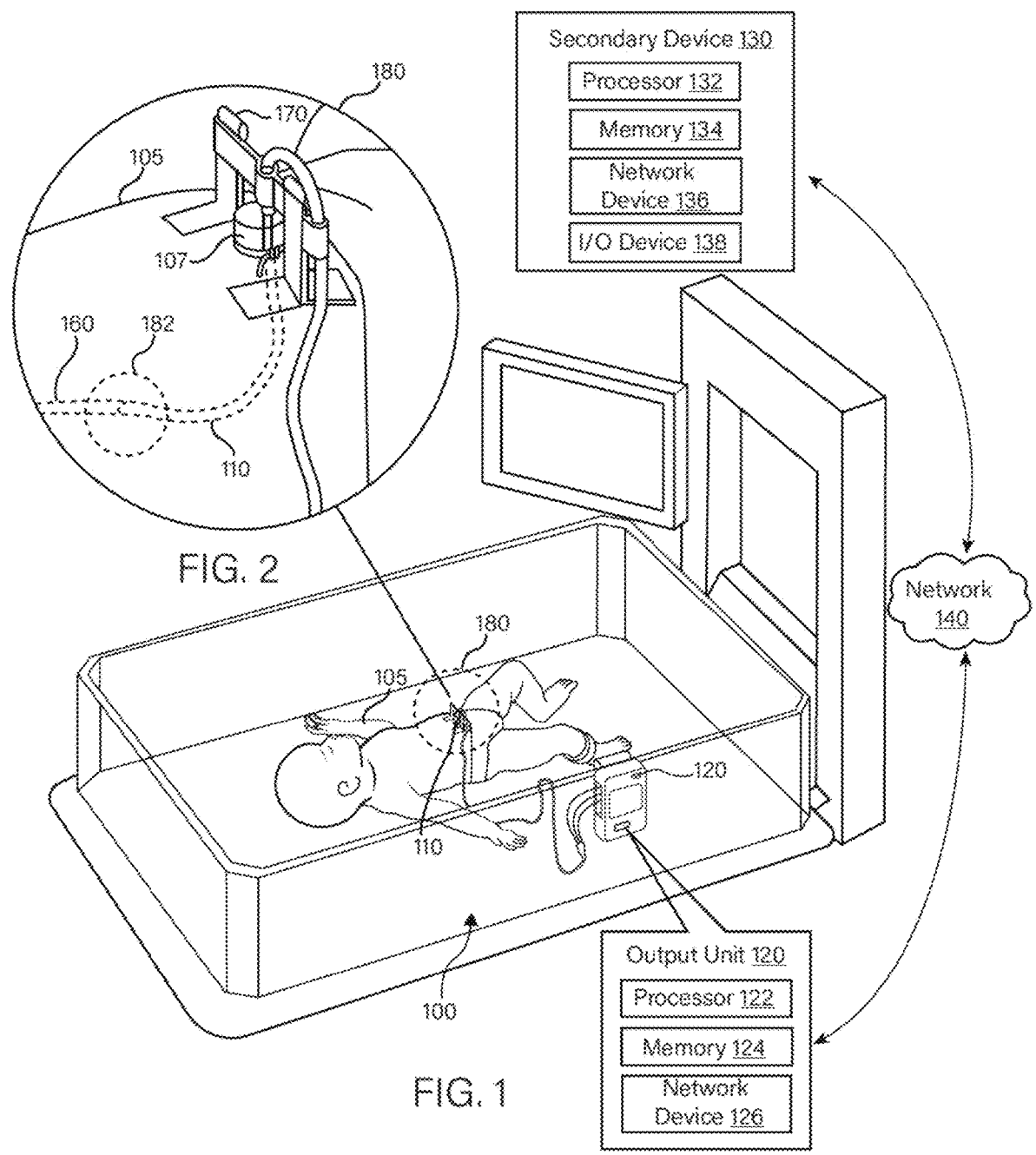
FIG. 1 illustrates a generalized representation of a system including a catheter in accordance with some embodiments.
FIG. 2 is an enlarged perspective view of a catheter shown to be inserted into a body of a patient in accordance with some embodiments.

In the following description, reference is made to the accompanying drawings which form a part of this application and which illustrate several embodiments of the present invention. It is understood that other embodiments may be utilized and structural and operational changes may be made without departing from the scope of the present invention.

Referring generally to the figures, embodiments described herein relate to a catheter (e.g., an umbilical catheter) configured to be inserted into a body (e.g., a navel) of a patient (e.g., a neonate) for continuous monitoring of blood gas parameters (e.g., $PaO_2$, $PaCO_2$, bicarbonate, pH, temperature, a combination thereof, and/or the like) in real-time. That is, the catheter as described herein may include one or more optical sensors embedded or otherwise incorporated into an umbilical catheter.

In some embodiments, the catheter may include distributed fiber optic gas sensors with a functionalized cladding layer for continuous sensing over a selected length of the optical fiber. Multiple sensing spots in a given area can provide stable readings, even as the patient moves. For instance, various distributed fiber optic sensors for measuring the blood gas parameters may provide large sensing areas on the optical fiber to avoid specific and limited placement of the sensing areas, therefore making the measured values immune to the "wall effect."

In some embodiments, two or more sensors (e.g., redundant $O_2$ sensors) may be used to avoid the "wall effect" in the manner described. For instance, two redundant $O_2$ sensors may be positioned on opposite sides with respect to a diameter of a cross section of a sensitive segment of an optical fiber to ensure that at least one of the two redundant $O_2$ sensors may be exposed to the bloodstream at any given time for continuous read-outs, even though one of the redundant $O_2$ sensors may contact the arterial vascular wall.

In some embodiments, a processor managing or otherwise processing outputs of the blood gas parameter sensors may determine that the "wall effect" is occurring in response to determining a "$O_2$ sensor reading down" pattern (e.g., fluctuations in sensor reading due to the "wall effect"). For example, this can be accomplished by correlating the readings with known "$O_2$ sensor reading down" patterns. The "wall effect," according to multiple clinical trials of intravascular sensors, affects $O_2$ measurements and does not interfere with the pH or $PaCO_2$ measurements. Responsive to determining that the "wall effect" is occurring, the processor may be configured to filter out or otherwise omit the erroneous reading from one of the redundant $O_2$ sensors during data fusion. Accordingly, reliable and stable values for the blood gas parameters can be attained.

In some embodiments, using emission lifetime measurements instead of amplitude measurements used in previously commercialized sensor systems can result in stable and reliable measurements, such that the catheter as described herein requires no further calibration after initial calibration at the time of manufacturing.

As referred to herein, a blood gas parameter may refer to a parameter relating to one or more gases present in blood, such as, but not limited to, $O_2$, $CO_2$, bicarbonate, and the like. Examples of a blood gas parameter may include, but not be limited to, $PaO_2$, $PaCO_2$, bicarbonate, pH, temperature, and the like. As referred to herein, a blood gas parameter sensor may refer to a sensing element for sensing one or more of the blood gas parameters. In some examples, the blood gas parameter sensors may be various fiber optic gas sensors.

FIG. 1 illustrates a generalized representation of a system 100 including a catheter 110 in accordance with some embodiments. Referring to FIG. 1, the catheter 110 may be an Integrated Fiber Optic Sensor Umbilical (ISUM) Catheter as described herein. The catheter 110 may be inserted into a body of a patient 105. In the non-limiting example illustrated by FIG. 1, the patient 105 may be a neonate. One of ordinary skill in the art can appreciate that the catheter 110 can be configured for other patients of different ages, genders, and/or physical conditions.

The catheter 110 may be connected or otherwise operatively coupled to an output unit 120. The output unit 120 may be computing or processing device configured to receive output data from the catheter 110. The output unit 120 may manage or process at least a portion of the output data provided by the catheter 110 (and a photo detector associated therewith). In some embodiments, the output unit 120 may relay the output data to a secondary device 130 over a network 140 for display or further processing.

In some embodiments, the output unit 120 may be a desktop computer, mainframe computer, laptop computer, pad device, smart phone device, processor unit, or the like configured with hardware and software to perform operations described herein. For example, the output unit 120 may be a processing device configured to be fastened or otherwise secured to a bed on which the patient 105 lies and may have suitable processing capabilities, memory, user interface (e.g., display and input) capabilities, and communication capabilities, when configured with suitable application software (or other software) to perform operations described herein. Thus, particular embodiments may be implemented, using processor devices that are often already present for a typical intravascular catheter or umbilical arterial catheter, by configuring such devices with suitable software processes described herein. Accordingly, such embodiments may be implemented with minimal additional hardware costs. However, other embodiments of the backend device 110 may relate to systems and processes that are implemented with dedicated device hardware specifically configured for performing operations described herein relative to sensing the blood gas parameters.

The processor 122 may include any suitable data processing device, such as a general-purpose processor (e.g., a microprocessor), but in the alternative, the processor 122 may be any conventional processor, controller, microcontroller, or state machine. The processor 122 may also be implemented as a combination of computing devices, e.g., a combination of a DSP and a microprocessor, a plurality of microprocessors, at least one microprocessor in conjunction with a Digital Signal Processing (DSP) core, or any other such configuration. The memory 124 may be operatively coupled to the processor 122 and may include any suitable device for storing software and data for controlling and use by the processor 122 to perform operations and functions described herein, including, but not limited to, Random Access Memory (RAM), Read Only Memory (ROM), floppy disks, hard disks, dongles or other Recomp Sensor Board (RSB) connected memory devices, or the like.

The network device 126 may include interface software, hardware, or combinations thereof, for connection with and communication over the network 140. The network device 126 may include wireless receiver or transceiver electronics and/or software that provides a wireless communication link with the network 140 (or with a network-connected device). In particular embodiments, the network device 126 may operate with the processor 122 for providing wireless communication functions. The wireless device 126 may provide communications in accordance with typical industry standards, such as, but not limited to, Code Division Multiple Access (CDMA), Time Division Multiple Access (TDMA), Frequency Division Multiple Access (FDMA), Long Term Evolution (LTE), Wireless Fidelity (WiFi), Frequency Modulation (FM), Bluetooth (BT), Near Field Communication (NFC), and the like. In other examples, the network device 126 may enable communications via a wired connection (e.g., Ethernet) to the network 140.

In some embodiments, the network 140 may allow data transfer between the output unit 120 and the secondary device 130. The network 140 may be any suitable wired or wireless network. In particular embodiments, the network 140 may represent one or more secure networks configured with suitable security features, such as, but not limited to, firewalls, encryption, or other software or hardware configurations that inhibit access to network communications by unauthorized personnel or entities.

The secondary device 130 may include at least a processor 132, memory 134, network device 136, and input/output (I/O) device 138. The processor 132 may be a processor, such as, but not limited to, the processor 122. The memory 134 may be a memory such as, but not limited to, the memory 124. The network device 136 may be a device, such as, but not limited to, the network device 126.

The I/O device 138 may include at least one display device. The display device may include any suitable device that provides a human-perceptible visible signal, audible signal, tactile signal, or any combination thereof, including, but not limited to a touchscreen, LCD, LED, CRT, plasma, or other suitable display screen, audio speaker or other audio generating device, combinations thereof, or the like. The display device may be configured to display various information about the blood gas parameters. Illustrating with the non-limiting example presented in FIG. 1, the display device of the I/O device 138 may output real-time graphs showing one or more blood gas parameter values over time.

In some embodiments, the I/O device 138 may include at least one user input device that provides an interface for personnel (such as doctors, nurses, caretakers, and/or the like) to access the secondary device 130. The user input device may include any suitable device that can receive input from the personnel, including, but not limited to, one or more manual operator (such as, but not limited to, a switch, button, touchscreen, knob, slider or the like), microphone, camera, image sensor, or the like. The user input device may be configured to receive user input related to operating the catheter 110. In some embodiments, the I/O device 138 may be provided to the output unit 120 alternatively or in addition to being provided to the secondary device 130.

FIG. 2 is an enlarged perspective view 180 of the catheter 110 shown to be inserted into a body of the patient 105 in accordance with some embodiments. Referring to FIGS. 1-2, the catheter 110 may be inserted into the body of the patient 105 in a suitable manner to access a suitable artery (e.g., a central artery, femoral artery, umbilical artery, or the like). Illustrating with the non-limiting example set forth in FIG. 2, the catheter 110 may be inserted into a navel 107 of the patient 105 in a manner consistent with umbilical artery catheterization to access an artery 160 (e.g., an umbilical artery in abdominal and pelvic regions of the patient 105). In some embodiments, the catheter 110 may be supported or otherwise stabilized by a stand 170. The catheter 110 may be configured to remain in the artery 160 of the patient 105 for an extended period of time (e.g., for as long as needed to sample the one or more blood gas parameters) in a manner consistent with conventional umbilical catheters so as to enable continuous monitoring in real-time. This stands in contrast with point sensors that require instances of blood draw every time a blood gas parameter needs to be evaluated.

FIG. 3 is an enlarged perspective view 182 of the catheter 110 shown to be inserted into the artery 160 in accordance with some embodiments. FIG. 4 is an enlarged perspective view 184 of the catheter 110 in accordance with some embodiments. Referring to FIGS. 1-4, a portion of the artery 160 may be sectioned in FIG. 3 for clarity. A portion of a catheter wall 102 may be sectioned for clarity. The catheter 110 may include the catheter wall 102 that forms at least one lumen (e.g., a lumen 104) in an interior surface of the catheter wall 102. The lumen 104 may be a hollow channel within the catheter 110 configured for blood pressure monitoring, arterial blood sampling, blood transfusion, nutrition infusion, or the like. In other words, the lumen 104 may function as a part of umbilical arterial catheterization. While one lumen (e.g., the lumen 104) is shown in the non-limiting example set forth in FIG. 3, configurations with two or more lumens (e.g., defined by two interior surfaces of the catheter wall 102) having the same or different sizes may likewise be a part of the catheter 110. For instance, a primary lumen and secondary lumen may be provided to perform two of the blood pressure monitoring, arterial blood sampling, blood transfusion, and nutrition infusion, simultaneously.

At least one optical fiber (e.g., the optical fibers 220a, 220b, 220c, and 220d) may be embedded into the catheter wall 102. While four optical fibers (e.g., the optical fibers 220a, 220b, 220c, and 220d) are shown in the non-limiting example set forth in FIG. 4, one of ordinary skill in the art can appreciate that any number such optical fibers may be embedded in the catheter wall 102. Each optical fiber 220a, 220b, 220c, or 220d may be configured to detect a particular blood gas parameter. Each optical fiber 220a, 220b, 220c, or 220d may extend in a same direction as a direction in which the catheter 110 (e.g., the catheter wall 102) extends by virtue of the optical fibers 220a, 220b, 220c, and 220d being embedded into the catheter wall 102.

Each optical fiber 220a, 220b, 220c, or 220d may be incorporated or otherwise embedded into a sensorized lumen of the catheter wall 102. A sensorized lumen may be a lumen other than the lumen 104 (or any other lumen being used for umbilical arterial catheterization purposes). The sensorized lumen may be an open channel of a suitable shape consistent with that of each optical fiber 220a, 220b, 220c, or 220d embedded therein. The open channel may open at an exterior surface of the catheter wall 102. The exterior surface may be different from the interior surface of the catheter wall 102, where the interior surface may define the lumen 104. Examples of the length of the sensorized lumen (open channel) in the catheter wall 102 may include, but not be limited to, 10 mm, 15 mm, 20 mm, 25 mm, 30 mm, 10-30 mm, or the like.

Each optical fiber 220a, 220b, 220c, or 220d may be composed of silica, plastic, or another suitable material. In some examples, polymer material instead of silica may be used for each optical fiber 220a, 220b, 220c, or 220d for flexibility, robustness, and suitability for integration into the catheter 110. Each optical fiber 220a, 220b, 220c, or 220d may have a sensitive segment 200 and a transmission segment 210. In some embodiments, the sensitive segment 200 may on one end of each of the optical fibers 220a, 220b, 220c, or 220d in the artery 160. The sensitive segment 200 may conform to the length of the sensorized lumen in the catheter wall 102. For instance, examples of the length of the sensitive segment 200 may include, but not be limited to, 10 mm, 15 mm, 20 mm, 25 mm, 30 mm, 10-30 mm, or the like. The transmission segment 210 may bridge the sensitive segment 200 and a photodetector configured to record light sensed in the sensitive segment 200.

The sensitive segment 200 of each optical fiber 220a, 220b, 220c, or 220d may include various blood gas parameter sensors (e.g., blood gas parameter sensors 222a, 222b, or the like). The blood gas parameter sensors may be arranged in a distributed configuration and may thusly be called distributed fiber optic gas sensors. The distributed configuration may refer to various blood gas parameter sensors for a same blood gas parameter may be distributed along a length of the sensitive segment 200 of a given optical fiber 220a, 220b, 220c, or 220d, thus creating multiple sensing spots. The blood gas parameter sensors on a given optical fiber may be spaced apart from one another and can thus simultaneously detect the blood gas parameter along the length of the sensitive segment 200. The outputs from the blood gas parameter sensors on a given optical fiber may be combined to produce, in effect, a single output of a single sensing element (e.g., a single blood gas parameter sensor) with a length equal to that of the sensitive segment 200. The collected light output may be transmitted along the transmission segment 210 (as well as any other additional data transmission elements) to reach photodetector and the output unit 120.

Each blood gas parameter sensor may be a luminescent optical fiber chemical sensor, and may be a chemically-sensitive material in which specific types of luminescent indicator molecules have been immobilized in a polymer substrate (e.g., a dye-doped polymer or sensitive material). In response to determining a selective interaction between a target analyte (e.g., a blood gas, such as, but not limited to, $CO_2$, $O_2$, or the like, or pH) and the specific type of luminescent indicator molecules, the luminescence of the chemically-sensitive material may undergo a measurable change proportional to the concentration of the target analyte.

Figure 5:
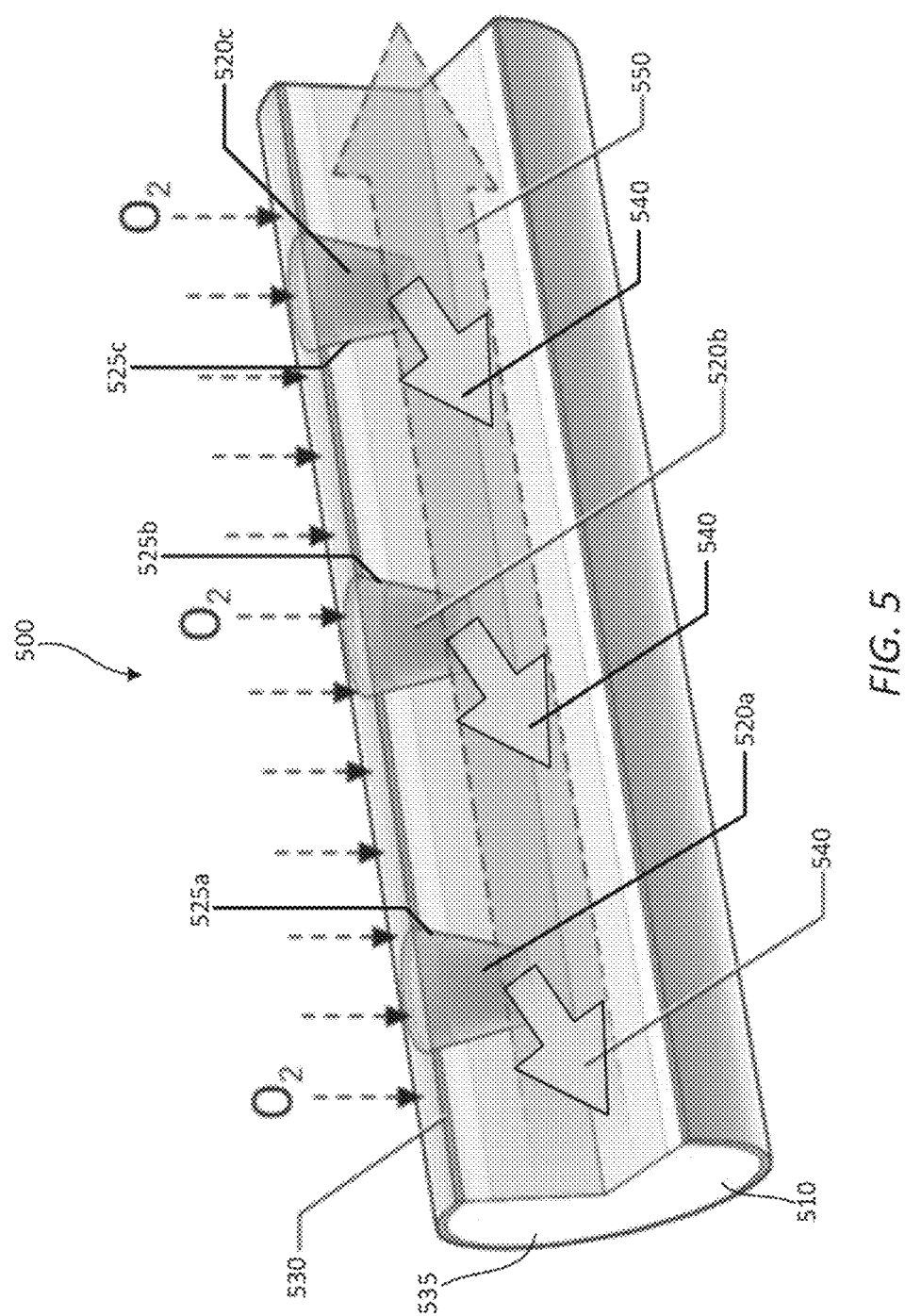
FIG. 5 is an enlarged perspective view of an optical fiber having a plurality of blood gas parameter sensors (distributed fiber optic gas sensors) embedded therein in accordance with some embodiments.

FIG. 5 is an enlarged perspective view 500 of an optical fiber 510 having a plurality of blood gas parameter sensors (distributed fiber optic gas sensors) 520a-520c embedded therein in accordance with some embodiments. Referring to FIGS. 1-5, the optical fiber 510 may be sectioned for clarity. In some embodiments, the optical fiber 510 may be one of the optical fibers 220a, 220b, 220c, and 220d of the catheter 110 that is integrated into the catheter wall 102. The presented perspective view 500 is of a sensitive segment (e.g., the sensitive segment 200) of the optical fiber 510. Each of the blood gas parameter sensors 520a-520c may be one of the blood gas parameter sensors 222a or 222b.

In the non-limiting example shown in FIG. 5, the optical fiber 510 may be cylindrical having a circular cross section. In other examples, the optical fiber 510 may be of any suitable shape, such as, but not limited to, oval, square, rectangle, irregular shape, or the like for the cross-section. The optical fiber 510 may have a functionalized cladding layer 530 covering at least the sensitive segment 200 of the optical fiber 510. The cladding layer 530 may cover or otherwise surround a core 535 of the optical fiber 510. The cladding layer 530 may be composed of a gas-permeable and water-impermeable polymer. The cladding layer 530 may be composed of polymethyl-methacrylate (PMMA). The core 535 may be composed of polystyrene.

In a fabrication process, portions of the cladding layer 530 and the core 535 may be precisely removed or otherwise drilled out at spots by a laser beam, thus creating wells 525a-525c along the sensitive segment 200 of the optical fiber 510. Each of the blood gas parameter sensors 520a-520c may be located in one of the wells 525a-525c, respectively. The length of the sensitive segment 200, depth, shape, size, number of the wells 525a-525c, and/or distance between the wells 525a-525c may be tuned according to sensor application. While in the non-limiting example presented by FIG. 5, three blood gas parameter sensors 520a-520c are shown for illustrative purposes, one of ordinary skill in the art can appreciate that more or less blood gas parameter sensors 520a-520c may be provided to the optical fiber 510 and tuned in the manner described. Illustrating with a non-limiting example, 5 blood gas parameter sensors (each of which may be a sensor, such as, but not limited to, the blood gas parameter sensors 520a-520c) may be distributed along a sensitive segment 200 having a length of 10 mm.

The wells 525a-525c may be filled with sensitive material (e.g., the chemically-sensitive material in which specific types of luminescent indicator molecules have been immobilized in a polymer substrate (e.g., a dye-doped polymer or sensitive material) to form the blood gas parameter sensors 520a-520c.

In some examples, to fabricate the materials sensitive to $O_2$, ion tris(4,7-diphenyl-1,10-phenanthroline)ruthenium (II), $(Ru(dip)_3)^{2+}$ may be incorporated or otherwise integrated into room-temperature vulcanized (RTV) silicone rubber. Given that the emission lifetime of $(Ru(dip)_3)^{2+}$ may depend on $O_2$ concentration level, phase-resolved luminescence detection may be implemented for the intravascular gas monitoring. The RTV silicone rubber has properties of hydrophobicity (blood impermeability) and high gas permeability. The $O_2$ dissolved in blood permeates the doped polymeric material, quenching the luminescence of $(Ru(dip)_3)^{2+}$. In some examples, dye and the blood does not contact one another, and no indicator leakage is possible.

In some examples, HPTS (8-hydroxypyrene-1,3,6-trisulfonic acid) and Oregon Green® 514 carboxylic acid may be used to fabricate the materials sensitive to pH. Poly(hydroxilethylmethacrylate) (pHEMA) may be a polymeric material with high water absorption and permeability and may be essential for indicator/sensor interaction with the blood. By properly selecting cross linker and incorporating vinyl imidazole as co-monomer, material porosity and water absorption may be controlled to ensure total retention of pH indicator in the polymer matrix. A strong interaction between anionic groups of the pH indicator (sulfonic or carboxylic) and the imidazole group in the co-monomer may be responsible for retention of the pH indicator.

The cladding layer (e.g., the cladding layer 530) may be embedded with a chemical mixture optically sensitive to pH variations. Diffusion of $CO_2$ molecules into the sensitive material along with subsequent hydration may generate carbonic acid. The resulting change in the sensitive material may be detected by monitoring emission of the optical indicator. The cladding layer may act as a separation layer that absorbs $CO_2$ molecules and may prevent interaction of the indicator with the blood. Thus, the sensitive material may not be affected by pH variations, salts, or other ions dissolved in the blood.

After the sensitive material has been filled in the wells 525a-525c and the optical fiber 510 (with the sensitive material) has been embedded into the open channel (e.g., the sensorized lumen), the blood gas parameter sensors 520a-520c and a portion of the sensitive segment 200 may be exposed by the catheter wall 102 for sensing the analyte (e.g., $O_2$ in the non-limiting example presented by FIG. 5).

The (open channel) with the blood gas parameter sensors 520a-520c and the portion of the sensitive segment 200 exposed may be coated with or otherwise covered by a biocompatible, medical grade permeable material that can allow light of the analyte to pass through to the blood gas parameter sensors 520a-520c. In some examples, the permeable material can (1) avoid blood flow artifacts by maintaining the shape (e.g., the cylindrical shape) of the catheter 110; (2) assure biocompatibility of the sensitive segment 200 and/or the blood gas parameter sensors 520a-520c; and/or (3) prevent clotting on the blood gas parameter sensors 520a-520c, for example, by incorporating heparin, which has been proven effective for intravascular monitoring devices and delaying biofouling. In some examples, silicone may be the permeable material of choice for covering $O_2$ and/or $CO_2$ blood gas parameter sensors given its high gas permeability. In some examples, various hydrogel-based polymeric materials may be the permeable material of choice for cover pH blood gas parameter sensors given its permeability to hydronium cation (pH).

Accordingly, the blood gas parameter sensors 520a-520c may be placed in a path of light transmitted through the optical fiber 510. A light source (e.g., from $O_2$) may excite fluorescence of the dye-doped polymer of the blood gas parameter sensors 520a-520c in the wells 525a-525c. While in the non-limiting example presented by FIG. 5, $O_2$ molecules are shown for illustrative purpose, one of ordinary skill in the art can appreciate that other blood gases (analytes), such as, but not limited to, $CO_2$ and pH to which sensor materials can be tuned may be detected in a similar manner. All the blood gas parameter sensors 520a-520c may be excited simultaneously by the associated analyte along the length of the sensitive segment 200. Emission of the dye-doped polymer of the blood gas parameter sensors 520a-520c may be transferred into the core 535 and transmitted along the sensitive segment 200 (e.g., the permeable segment) and the transmission segment 210 to reach the photodetector. For example, orange emission may travel along a first path 540 and blue excitation may travel along a second path 550. The photodetector may record the light received and relay the measurements to the output unit 120. The photodetector may be placed in any suitable location, such as, but not limited to, in the output unit 120, supported by the stand 170, or the like.

Distributing the blood gas parameter sensors 520a-520c along the sensitive segment 200 of the optical fiber 510 can increase effective sensitive area (associated with the sensitive segment 200) and allow for a stable reading even during patient movement, given that the patient movement may effect some but not all of the blood gas parameter sensors. For example, Even in the event that some of the blood gas parameter sensors 520a-520c contact the vascular wall, other ones of the blood gas parameter sensors 520a-520c along the sensitive segment 200 (which may be as long as 30 mm) may still produce accurate readings, despite that each individual one of the blood gas parameter sensors 520a-520c may be in the scale of microns. For a sensitive segment 200 having a length of 20 mm, the effective sensing length is 100 times longer than point sensors. Thus, specific position of the optical fiber 510 or the "wall effect" does not affect the combined readings of the blood gas parameter sensors 520a-520c embedded in the optical fiber 510.

Figure 6B:
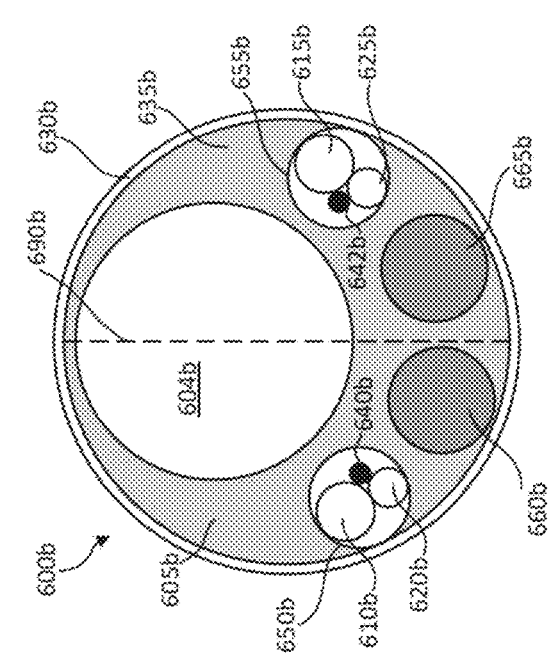
FIG. 6B is a cross-section of an example of a catheter according to various embodiments.
Figure 6D:
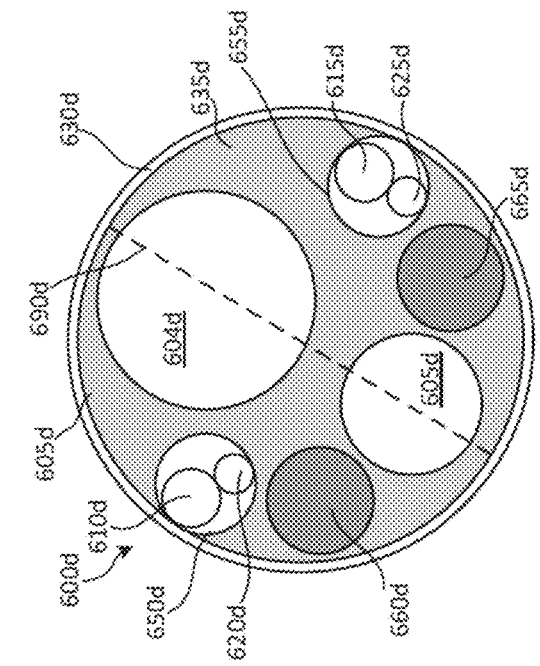
FIG. 6D is a cross-section of an example of a catheter according to various embodiments.
Figure 6A:
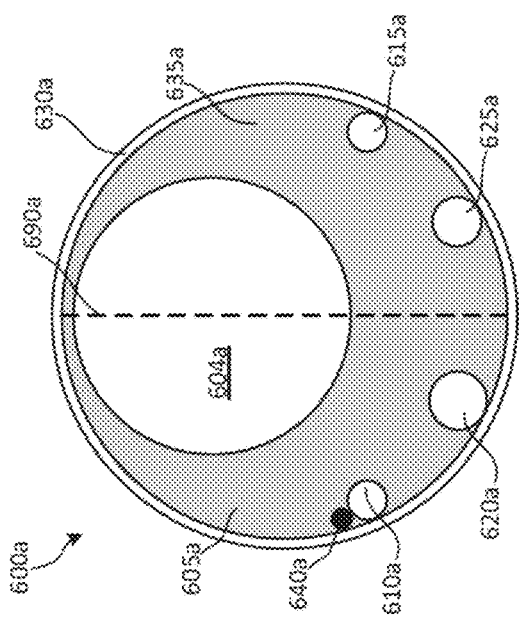
FIG. 6A is a cross-section of an example of a catheter according to various embodiments.

FIG. 6A may be a cross-section 600a of an example of a catheter 605a (e.g., the catheter 110 of FIGS. 1-4) according to various embodiments. Referring to FIGS. 1-6A, the cross section 600a may show cross-sections of optical fibers 610a, 615a, 620a, and 625a, and temperature sensor 640a. In particular, the sensitive segment 200 of each optical fiber 610a, 615a, 620a, or 625a may be shown, with the embedded sensors (e.g., the blood gas parameter sensors 222a, 222b, 525a-525c, or the like) omitted for the sake of clarity. The transmission segment 210 (without any of the embedded sensors) of each optical fiber 610a, 615a, 620a, or 625a may appear in a similar manner in cross-sectional views.

The catheter 605a may include a catheter wall 635a such as, but not limited to, the catheter wall 102. The catheter 605a may include a permeable material 630a such as, but not limited to, the biocompatible, medical grade permeable material that can allow the light of the analyte to pass through to the blood gas parameter sensors on each of the optical fibers 610a, 615a, 620a, and 625a. The catheter 605a may include a lumen 605a (such as, but not limited to, the lumen 104) configured for umbilical arterial catheterization. For instance, the lumen 605a may have a diameter of 0.9-1.2 mm. Each of the optical fibers 610a, 615a, 620a, and 625a may be integrated or otherwise embedded into a sensorized lumen of the catheter wall 635a.

The catheter 605a may include a temperature sensor 640a for sensing temperature in a manner described. The temperature sensor 640a may be a (miniature) thermocouple element. The diameter of the temperature sensor 640a may be 0.05 mm or 0.075 mm. The catheter 605a may include a $CO_2$-sensing optical fiber 620a having blood gas parameter sensors embedded therein for sensing $PaCO_2$ in a manner described. The diameter of the $CO_2$-sensing optical fiber 620a may be 0.15-0.2 mm. The catheter 605a may include a pH-sensing optical fiber 625a having blood gas parameter sensors embedded therein for sensing pH in a manner described. The diameter of the pH-sensing optical fiber 625a may be 0.15-0.2 mm.

The catheter 605a may include two $O_2$-sensing optical fibers 610a and 615a having blood gas parameter sensors embedded therein for sensing $PaO_2$ in a manner described. The diameter of each of the $O_2$-sensing optical fibers 610a and 615a may be 0.15-0.2 mm. The two $O_2$-sensing optical fibers 610a and 615a may be collectively referred to as redundant $O_2$ sensors and may be located on opposite sides of the cross-section 600a of the catheter 605a. Illustrating with the non-limiting example of FIG. 6A, the $O_2$-sensing optical fibers 610a and 615a may be located opposite to one another in the cross section 600a relative to (e.g., symmetrical relative to) a diameter 690a of the cross section 600a. In some examples, centers of the $O_2$-sensing optical fibers may be located on a first diameter of the cross section 600a, and such $O_2$-sensing optical fibers may be symmetrical relative to a second diameter of the cross section 600a, where the first diameter and the second diameter are perpendicular to one another. In other examples, the $O_2$-sensing optical fibers may spaced apart (e.g., having a distance therebetween) in other suitable configurations along the exterior surface of the catheter wall 635a and contacting the permeable material 630a.

The purpose of the $O_2$-sensing optical fibers 610a and 615a being spaced apart or being symmetrical with respect to the diameter 690a is to avoid the "wall effect." For instance, in addition to the length of the sensitive segment 200 of the $O_2$-sensing optical fibers 610a and 615a, redundant $O_2$-sensing optical fibers 610a and 615a located on either side of the cross-section 600a of the catheter 110 may further minimize and eliminate the "wall effect." By having two $O_2$-sensing optical fibers 610a and 615a having sensors tuned to the same blood gas (e.g., $O_2$ in this case given susceptibility of $O_2$ to the "wall effect") located on opposite sides of the cross section 600a, even when a first one of the $O_2$-sensing optical fibers 610a and 615a (and the sensors embedded therein) may contact the vascular wall, a second one of the $O_2$-sensing optical fibers 610a and 615a can nevertheless be able to sample $O_2$ in the artery 160 because the second one of the $O_2$-sensing optical fibers 610a and 615a cannot contact the vascular wall if the first one of the $O_2$-sensing optical fibers 610a and 615a is contacting the vascular wall. This is because the diameter 690a of the cross-section 600a may be significantly smaller than an internal diameter of the artery, 160 (or any other arteries) which is typically greater than 4 mm even for neonates with a body length as short as 30 cm. Examples of the length of diameter 690a may include, but not be limited to, 1.2 mm for 3.5 FR catheters or 1.7 mm for 5 FR catheters, respectively.

FIG. 6B may be a cross-section 600b of an example of a catheter 605b (e.g., the catheter 110 of FIGS. 1-4) according to various embodiments. Referring to FIGS. 1-6B, FIG. 6B may illustrate an alternative design for a single-lumen catheter having one lumen (e.g., the lumen 604a or 604b) for umbilical arterial catheterization. The cross section 600b may show cross-sections of optical fibers 610b, 615b, 620b, and 625b. In particular, the sensitive segment 200 of each optical fiber 610b, 615b, 620b, and 625b may be shown, with the embedded sensors (e.g., the blood gas parameter sensors 222a, 222b, 525a-525c, or the like) omitted for the sake of clarity. The transmission segment 210 (without any of the embedded sensors) of each optical fiber 610b, 615b, 620b, and 625b may appear in a similar manner in cross-sectional views.

The catheter 605b may include a catheter wall 635b, such as, but not limited to, the catheter walls 102 and 635a. The catheter 605b may include a permeable material 630b, such as, but not limited to, the permeable material 630a. The catheter 605b may include a lumen 605b (such as, but not limited to, the lumens 104 and 605a) configured for umbilical arterial catheterization. The lumen 605b may have a diameter of 0.9-1.2 mm. Two or more of the optical fibers 610b, 615b, 620b, and 625b may be integrated or otherwise embedded into a same sensorized lumen 650b or 655b of the catheter wall 635b. For instance, the optical fibers 610b, and 620b, and temperature sensor 640b may be located within the lumen 650b. The optical fibers 615b, and 625b, and temperature sensor 642b may be located within the lumen 655b. An opening side of each lumen 650b or 655b may be covered by the permeable material 630b to allow the light of the analyte to pass through to be sensed by the optical fibers in a respective one of the lumens 650b and 655b.

The catheter 605b may include temperature sensors 640b and 642b, each of which may be a sensor, such as, but not limited to, the temperature sensor 640a. The catheter 605b may include a $CO_2$-sensing optical fiber 620b having blood gas parameter sensors embedded therein for sensing $PaCO_2$ in the manner described. The diameter of the $CO_2$-sensing optical fiber 620b may be 0.15-0.2 mm. The catheter 605b may include a pH-sensing optical fiber 625b having blood gas parameter sensors embedded therein for sensing pH in a manner described. The diameter of the pH-sensing optical fiber 625b may be 0.15-0.2 mm.

The catheter 605b may include two $O_2$-sensing optical fibers 610b and 615b having blood gas parameter sensors embedded therein for sensing $PaO_2$ in a manner described. The diameter of each of the $O_2$-sensing optical fibers 610b and 615b may be 0.15-0.2 mm. The two 02-sensing optical fibers 610b and 615b may be collectively referred to as redundant $O_2$ sensors and may be located on opposite sides of the cross-section 600b of the catheter 605b. Illustrating with the non-limiting example of FIG. 6B, the $O_2$-sensing optical fibers 610b and 615b may be located opposite to one another in the cross section 600b relative to (e.g., symmetrical relative to) a diameter 690b of the cross section 600b. In some examples, centers of the $O_2$-sensing optical fibers may be located on a first diameter of the cross section 600b, and such $O_2$-sensing optical fibers may be symmetrical relative to a second diameter of the cross section 600b, where the first diameter and the second diameter are perpendicular to one another. In other examples, the $O_2$-sensing optical fibers may be spaced apart (e.g., having a distance therebetween) along the exterior surface of the catheter wall 635b and contacting the permeable material 630b. In some embodiments, the lumens 650b and 655b may be spaced apart and/or symmetrical relative to the diameter 690b to assure that the $O_2$-sensing optical fibers 610b and 615b may be spaced apart and/or symmetrical in the manner described. The purpose of the $O_2$-sensing optical fibers 610b and 615b being spaced apart or being symmetrical with respect to the diameter 690b is to avoid the "wall effect." Examples of the diameter 690b may include 1.2 mm for 3.5 FR catheters or 1.7 mm for 5 FR catheters, respectively.

In some embodiments, the catheter 605b may include reinforcement elements 660b and 665b configured to reinforce the catheter 605b and the optical fibers 610b, 615b, 620b, and 625b. The composition of the reinforcement elements 660b and 665b may improve the structural integrity of the catheter 605b while maintaining flexibility.

Figure 6C:
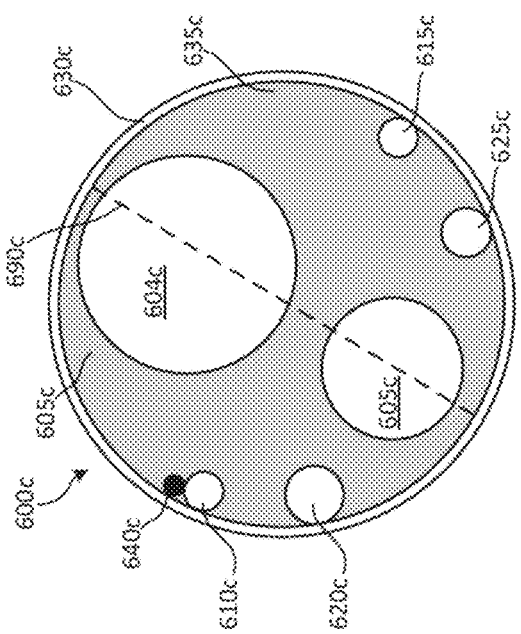
FIG. 6C is a cross-section of an example of a catheter according to various embodiments.

FIG. 6C may be a cross-section 600c of an example of a catheter 605c (such as, but not limited to, a catheter similar to the catheter 110 of FIGS. 1-4) according to various embodiments. Referring to FIGS. 1-6C, FIG. 6C may illustrate an alternative design for a catheter using a double-lumen configuration (e.g., lumens 604c and 605c). The cross section 600c may show cross-sections of optical fibers 610c, 615c, 620c, and 625c. In particular, the sensitive segment 200 of each optical fiber 610c, 615c, 620c, or 625c may be shown, with the embedded sensors (e.g., the blood gas parameter sensors 222a, 222b, 525a-525c, or the like) omitted for the sake of clarity. The transmission segment 210 (without any of the embedded sensors) of each optical fiber 610c, 615c, 620c, and 625c may appear in a similar manner in cross-sectional views.

The catheter 605c may include a catheter wall 635c, such as, but not limited to, the catheter walls 102, 635a, and 635b. The catheter 605c may include a permeable material 630c, such as, but not limited to, the permeable materials 630a and 630b. The catheter 605c may include a primary lumen 604c and a secondary lumen 605c, each of which may be configured for umbilical arterial catheterization, such as, but not limited to, the lumen 104. Each of the optical fibers 610c, 615c, 620c, and 625c may be integrated or otherwise embedded into a sensorized lumen of the catheter wall 635c.

The catheter 605c may include a temperature sensor 640c, such as, but not limited to, the temperature sensors 640a, 640b, and 642b. The diameter of the temperature sensor 640c may be 0.075 mm. The catheter 605c may include a $CO_2$-sensing optical fiber 620c having blood gas parameter sensors embedded therein for sensing $PaCO_2$ in a manner described. The diameter of the $CO_2$-sensing optical fiber 620c may be 0.15-0.2 mm. The catheter 605c may include a pH-sensing optical fiber 625c having blood gas parameter sensors embedded therein for sensing pH in a manner described. The diameter of the pH-sensing optical fiber 625c may be 0.15-0.2 mm.

The catheter 605c may include two $O_2$-sensing optical fibers 610c and 615c having blood gas parameter sensors embedded therein for sensing $PaO_2$ in a manner described. The diameter of each of the $O_2$-sensing optical fibers 610c and 615c may be 0.15-0.2 mm. The two 02-sensing optical fibers 610c and 615c may be collectively referred to as redundant $O_2$ sensors and may be located on opposite sides of the cross-section 600c of the catheter 605c. Illustrating with the non-limiting example of FIG. 6C, the $O_2$-sensing optical fibers 610c and 615c may be located opposite to one another in the cross section 600c relative to (e.g., symmetrical relative to) a diameter 690c of the cross section 600c. In some examples, centers of the $O_2$-sensing optical fibers may be located on a first diameter of the cross section 600c, and such $O_2$-sensing optical fibers may be symmetrical relative to a second diameter of the cross section 600c, where the first diameter and the second diameter are perpendicular to one another. In other examples, the $O_2$-sensing optical fibers may spaced apart (e.g., having a distance therebetween) along the exterior surface of the catheter wall 635c and contacting the permeable material 630c. The purpose of the $O_2$-sensing optical fibers 610c and 615c being spaced apart or being symmetrical with respect to the diameter 690c is to avoid the "wall effect." Examples of the diameter 690c may include 1.2 mm for 3.5 FR catheters or 1.7 mm for 5 FR catheters, respectively.

FIG. 6D may be a cross-section 600d of an example of a catheter 605d (e.g., the catheter 110 of FIGS. 1-4) according to various embodiments. Referring to FIGS. 1-6D, FIG. 6D may illustrate an alternative design for a double-lumen catheter having two lumens (e.g., lumens 604d or 605d) for conventional umbilical arterial catheterization. The cross section 600d may show cross-sections of optical fibers 610d, 615d, 620d, and 625d. In particular, the sensitive segment 200 of each optical fiber 610d, 615d, 620d, or 625d may be shown, with the embedded sensors (e.g., the blood gas parameter sensors 222a, 222b, 525a-525c, or the like) omitted for the sake of clarity. The transmission segment 210 (without any of the embedded sensors) of each optical fiber 610d, 615d, 620d, or 625d may appear in a similar manner in cross-sectional views.

The catheter 605d may include a catheter wall 635d, such as, but not limited to, the catheter walls 102, 635a, 635b, and 635c. The catheter 605d may include a permeable material 630d, such as, but not limited to, the permeable materials 630a, 630b, and 630d. The catheter 605d may include a primary lumen 604d (such as the primary lumen 604c) and a secondary lumen 605d (such as the secondary lumen 605c), each of which may be configured for umbilical arterial catheterization. Two or more of the optical fibers 610d, 615d, 620d, and 625d may be integrated or otherwise embedded into a same sensorized lumen 650d or 655d of the catheter wall 635d. For instance, the optical fibers 610d and 620d may be located within the lumen 650d. The optical fibers 615d and 625d may be located within the lumen 655d. An opening side of each lumen 650d or 655d may be covered by the permeable material 630d to allow the light of the analyte to pass through to be sensed by the optical fibers in a respective one of the lumens 650d and 655d.

The catheter 605d may include a $CO_2$-sensing optical fiber 620d having blood gas parameter sensors embedded therein for sensing $PaCO_2$ in a manner described. The diameter of the $CO_2$-sensing optical fiber 620d may be 0.15-0.2 mm. The catheter 605d may include a pH-sensing optical fiber 625d having blood gas parameter sensors embedded therein for sensing pH in a manner described. The diameter of the pH-sensing optical fiber 625d may be 0.15-0.2 mm. The catheter 605d may include temperature sensors (not shown), such as, but not limited to, the temperature sensors 640b and 642b.

The catheter 605d may include two $O_2$-sensing optical fibers 610d and 615d having blood gas parameter sensors embedded therein for sensing $PaO_2$ in a manner described. The diameter of each of the $O_2$-sensing optical fibers 610d and 615d may be 0.15-0.2 mm. The two $O_2$-sensing optical fibers 610d and 615d may be collectively referred to as redundant $O_2$ sensors and may be located on opposite sides of the cross-section 600d of the catheter 605d. Illustrating with the non-limiting example of FIG. 6D, the $O_2$-sensing optical fibers 610d and 615d may be located opposite to one another in the cross section 600d relative to (e.g., symmetrical relative to) a diameter 690d of the cross section 600d. In some examples, centers of the $O_2$-sensing optical fibers may be located on a first diameter of the cross section 600d, and such $O_2$-sensing optical fibers may be symmetrical relative to a second diameter of the cross section 600d, where the first diameter and the second diameter are perpendicular to one another. In other examples, the $O_2$-sensing optical fibers may spaced apart (e.g., having a distance therebetween) along the exterior surface of the catheter wall 635d and contacting the permeable material 630d. In some embodiments, the lumens 650d and 655d may be spaced apart and/or symmetrical relative to the diameter 690d to assure that the $O_2$-sensing optical fibers 610d and 615d may spaced apart and/or symmetrical in the manner described.

The purpose of the $O_2$-sensing optical fibers 610d and 615d being spaced apart or being symmetrical with respect to the diameter 690d is to avoid the "wall effect." Examples of the diameter 690d may include 1.2 mm for 3.5 FR catheters or 1.7 mm for 5 FR catheters, respectively.

Figure 7:
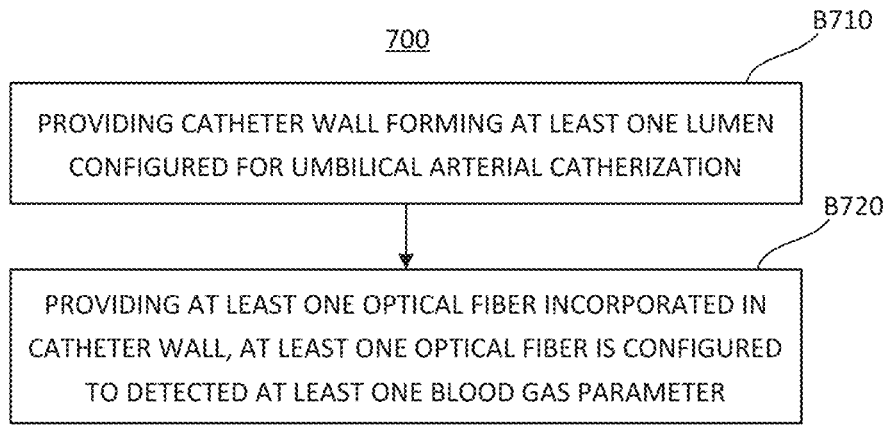
FIG. 7 is a process flowchart diagram illustrating an example of a method for providing a catheter configured to detect at least one blood gas parameter present in an artery of a patient according to various embodiments.

In some embodiments, the catheter 605d may include reinforcement elements 660d and 665d configured to reinforce the catheter 605d and the optical fibers 610d, 615d, 620d, and 625d. The reinforcement elements 660d and 665d may be similar to the reinforcement elements 660b and 665b FIG. 7 is a process flowchart diagram illustrating an example of a method 700 for providing a catheter (e.g., the catheter 110 of FIGS. 1-4) configured to detect at least one blood gas parameter present in an artery (e.g., the artery 160 of FIGS. 2-3) of a patient (e.g., the patient 105 of FIGS. 1-2) according to various embodiments. Referring to FIGS. 1-7, at block B710, the catheter wall 102 that forms at least one lumen (e.g., the lumens 104, 604a, 604b, 604c, 605c, 604d, and/or 605d) configured for umbilical arterial catheterization is provided. At block B720, at least one optical fiber (e.g., the optical fibers 220a, 220b, 510, 610a, 615a, 620a, 625a, 610b, 615b, 620b, 625b, 610c, 615c, 620c, 625c, 610*d*, 615*d*, 620*d*, and/or 625*d*) incorporated in the catheter wall 102 may be provided. The at least one optical fiber may be configured to detected the at least one blood gas parameter.

Figure 8:
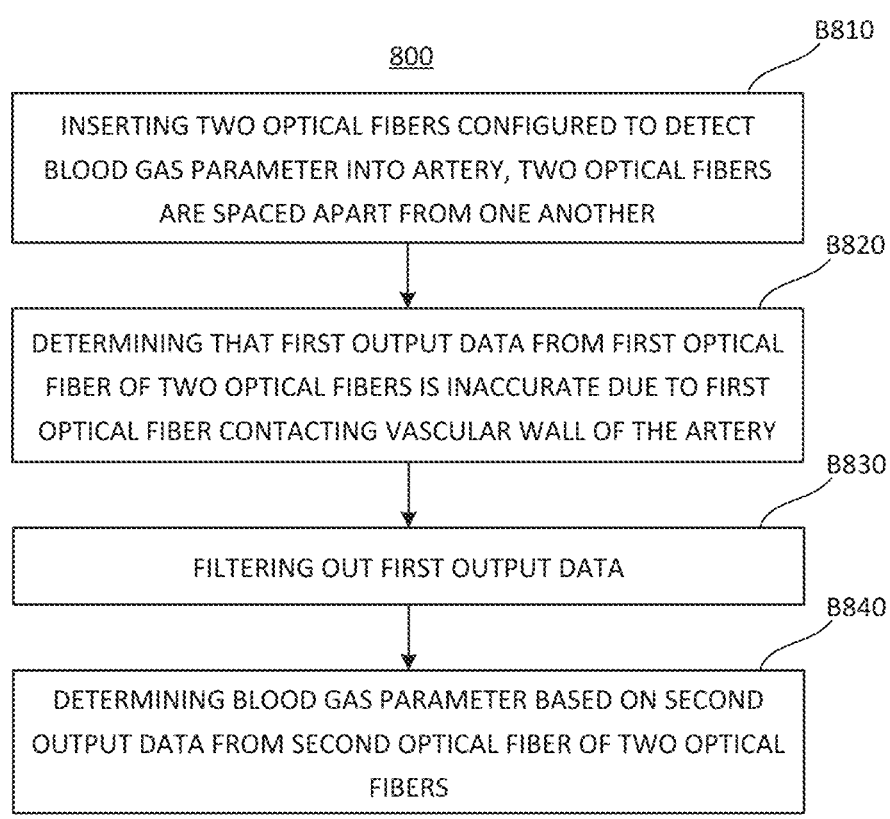
FIG. 8 is a process flow chart diagram illustrating an example of a method for determining a blood gas parameter present in blood in an artery of a patient according to various embodiments.

FIG. 8 is a process flowchart diagram illustrating an example of a method 800 for determining a blood gas parameter present in blood in an artery (e.g., the artery 160 of FIGS. 2-3) of a patient (e.g., the patient 105 of FIGS. 1-2) according to various embodiments. Referring to FIGS. 1-8, at block B810, two optical fibers (e.g., the optical fibers 610*a* and 615*a*, or 610*b* and 615*b*, or 610*c*, and 615*c*, or 610*d* and 615*d*) configured to detect the blood gas parameter may be inserted into the artery 160. The two optical fibers are spaced apart from one another in the manner described to avoid the "wall effect." First output data from a first optical fiber (e.g., the optical fiber 610*a*, 610*b*, 610*c*, or 610*d*) and second output data from a second optical fiber (e.g., the optical fiber 615*a*, 615*b*, 615*c*, or 615*d*) may be fused together to determine the blood gas parameter. That is, the light detected by the sensitive segment 200 of each of the first and second optical fibers is transmitted through each respective transmission segment 210 to a photodetector which records the readings and sends the readings to the output unit 120. The output unit 120 may perform the combination/fusion of the first output data and the second output data by the processor 122, or alternatively, the network device 126 may send the readings to the secondary device 130 such that the processor 132 may perform the combination/fusion.

At block B820, the processor 122 or the processor 132 may determine that the first output data from the first optical fiber of the two optical fibers is inaccurate due to the first optical fiber contacting a vascular wall of the artery 160. For instance, the first output data may be determined to be inaccurate in response to determining a sensor reading-down pattern (frequent, unpredictable, and/or sharp drops in $PaO_2$) associated with the first optical fiber contacting the vascular wall (e.g., the "wall effect"). At block B830, the processor 122 or the processor 132 may filter out the first output data. At block B840, the processor 122 or the processor 132 may determine the blood gas parameter based on the second output data from the second optical fiber of the two optical fibers.

Figure 9:
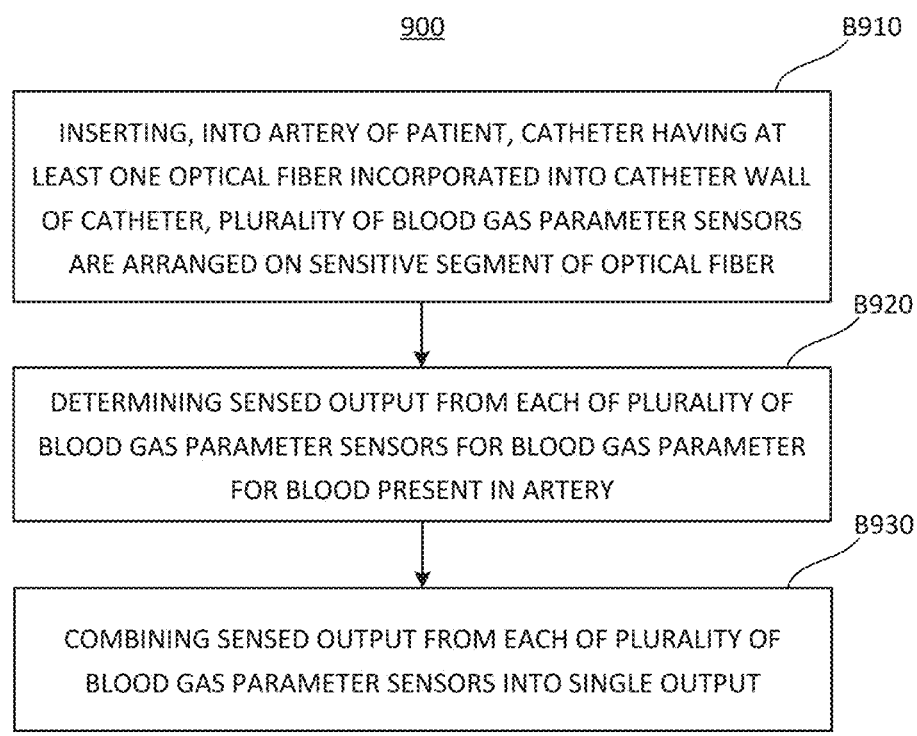
FIG. 9 a process flow chart diagram illustrating an example of a method for measuring one or more blood gas parameters.

FIG. 9 is a process flowchart diagram illustrating an example of a method 900 for measuring one or more blood gas parameters. Referring to FIGS. 1-9, at block B910, the catheter 110 having at least one optical fiber incorporated into a catheter wall of the catheter inserting, into an artery of a patient, a catheter having at least one optical fiber (e.g., the optical fiber 220*a*, 220*b*, 510, 610*a*, 615*a*, 620*a*, 625*a*, 610*b*, 615*b*, 620*b*, 625*b*, 610*c*, 615*c*, 620*c*, 625*c*, 610*d*, 615*d*, 620*d*, and/or 625*d*) incorporated into the catheter wall 102. A plurality of blood gas parameter sensors (e.g., the blood gas parameter sensors 222*a*, 222*b*, 520*a*, 520*b*, or 520*c*) may be arranged on the sensitive segment 200 of the optical fiber.

At block B920, a sensed output (e.g., measured light) from each of the plurality of blood gas parameter sensors may be determined for a blood gas parameter for blood present in the artery 160. At block B930, the sensed output from each of the plurality of blood gas parameter sensors may be combined into a single output. For instance, light sensed by each of the plurality of blood gas parameter sensors may travel through the sensitive segment 200 and transmission segment 210 to reach a photodetector configured to recording light sensed by the plurality of blood gas parameter sensors.

According to the description herein, the catheter 110 (e.g., the ISUM catheter) have been shown to have excellent precision. For instance, for a precision of 3 mmHg $PaO_2$ at 150 mmHg, a response time faster than 5 seconds (e.g., 2 seconds determined in atmosphere) may be demonstrated with respect to an optical fiber having a plurality of blood gas parameter sensors tuned to $O_2$. For a precision of 0.5 mmHg $PaCO_2$ at 7.5 mmHg and a precision of 3 mmHg $PaCO_2$ at 45 mmHg a response time faster than 10 seconds (e.g., 5 seconds determined in atmosphere) may be demonstrated. Catheter safety has been demonstrated by hemocompatibility and absence of thrombogenicity.

Laboratory results have shown excellent correlation with the gold-standard blood gas analysis technique. Safety was also confirmed. Accordingly, the catheter described herein bridges an important gap in critical care for neonates by allowing for the continuous monitoring of the blood gas parameters. The catheter as described can allow for early detection and instant intervention in response to determining deviations of one or more blood gas parameters from the norm given that the blood gas parameters are monitored continuously and in real-time. This can lead to quicker ventilator weans, early and more effective interventions in life-threatening emergencies such as air leaks, blocked endotracheal tubes, accidental extubations, and, due to reduced line-breaks, reduction in catheter-related line infections.

The catheter as described herein can reduce a healthcare provider's exposure to blood and reduce blood draws, which in turn reduces the need to blood transfusion and pain, protecting the chances of the treated neonates for long-term development. Overall, morbidity and mortality in critically sick neonates can be drastically reduced. The cost associated with repeated blood sampling in conventional methods can also be reduced. In some cases, reductions in retinopathy of prematurity and intra-periventricular bleeds may also be observed.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. Various modifications and changes that come within the meaning and range of equivalency of the claims are intended to be within the scope of the invention.

The foregoing method descriptions and the process flow diagrams are provided merely as illustrative examples and are not intended to require or imply that the steps of various examples must be performed in the order presented. As will be appreciated by one of skill in the art the order of steps in the foregoing examples may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the examples disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present examples.

The hardware used to implement the various illustrative logics, logical blocks, modules, and circuits described in connection with the examples disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In some exemplary examples, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in a processor-executable software module which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer program product.

The preceding description of the disclosed examples is provided to enable any person skilled in the art to make or use the present examples. Various modifications to these examples will be readily apparent to those skilled in the art, and the generic principles defined herein may be applied to some examples without departing from the spirit or scope of the examples. Thus, the present examples are not intended to be limited to the examples shown herein but are to be accorded the widest scope consistent with the following claims and the principles and novel features disclosed herein.

What is claimed is:

1. A catheter configured to detect at least one blood gas parameter present in blood in a blood vessel of a patient, comprising:
   a catheter wall forming at least one lumen configured for catheterization; and
   at least one optical fiber incorporated on an exterior surface of the catheter wall, wherein the at least one optical fiber comprising at least one blood gas parameter sensor configured to detect the at least one blood gas parameter.

2. The catheter of claim 1, wherein:
   the at least one lumen is formed in an interior surface of the catheter wall.

3. The catheter of claim 1, wherein:
   the at least one lumen is two or more lumens; and
   each of the at least one lumen is formed in an interior surface of the catheter wall.

4. The catheter of claim 1, wherein each of the at least one lumen is configured to perform one of blood pressure monitoring, arterial blood sampling, blood transfusion, or nutrition infusion.

5. The catheter of claim 1, wherein:
   the catheter wall comprises at least one open channel; and
   each of the at least one optical fiber is embedded in one of the at least one open channel.

6. The catheter of claim 1, wherein the at least one blood gas parameter comprises one or more of $PaO_2$, $PaCO_2$, bicarbonate, pH, or temperature.

7. The catheter of claim 1, wherein:
   each of the at least one optical fiber has a sensitive segment;
   a plurality of blood gas parameter sensors are arranged on the sensitive segment; and
   each of the plurality of blood gas parameter sensors on one of the at least one optical fiber is configured to detect one of the at least one blood gas parameter.

8. The catheter of claim 7, wherein each of the plurality of blood gas parameter sensors is a luminescent optical fiber chemical sensor tuned to the one of the at least one blood gas parameter.

9. The catheter of claim 7, wherein a plurality fiber optic distributed sensor comprising:
   an optical fiber wherein the optical fiber is fabricated with a series of wells into at least the cladding of the optical fiber, and wherein the wells have been filled with at least one material sensitive to a target blood gas parameter to form sensor wells.

10. The catheter of claim 1, wherein the at least one optical fiber comprises:
    a first optical fiber having a first plurality of blood gas parameter sensors configured to detect a first blood gas parameter of the at least one blood gas parameter; and
    a second optical fiber having a second plurality of blood gas parameter sensors configured to detect a second blood gas parameter of the at least one blood gas parameter.

11. The catheter of claim 1, wherein the at least one optical fiber comprises:
    two $O_2$-sensing optical fibers each having a plurality of blood gas parameter sensors configured to detect $PaO_2$;
    a $CO_2$-sensing optical fiber having a plurality of blood gas parameter sensors configured to detect $PaCO_2$; and
    a pH-sensing optical fiber having a plurality of blood gas parameter sensors configured to detect pH.

12. The catheter of claim 11, wherein the catheter further comprises a thermocouple incorporated in the catheter wall configured to detect temperature in the blood of the blood vessel.

13. The catheter of claim 1, wherein:
the catheter wall forms at least one sensorized lumen on the exterior surface of the catheter wall; and
each of the at least one optical fiber is embedded in one of the at least one sensorized lumen.

14. The catheter of claim 1, wherein:
the catheter wall forms at least one sensorized lumen on the exterior surface of the catheter wall;
the at least one optical fiber comprises two or more optical fibers; and
two or more of the at least one optical fiber are embedded in one of the at least one sensorized lumen.

15. The catheter of claim 1, wherein:
the at least one optical fiber comprises a first optical fiber configured to detect a first blood gas parameter of the at least one blood gas parameter and a second optical fiber configured to detect the first blood gas parameter; and
the first optical fiber and second optical fiber are located on opposite sides of a cross-section of the catheter relative to a diameter of the cross-section.

16. The catheter of claim 15, wherein the first optical fiber and the second optical fiber are symmetrically located in the cross-section relative to the diameter of the cross-section.

17. The catheter of claim 1, wherein the at least one optical fiber is configured to remain in the blood vessel for continuously detecting the at least one blood gas parameter.

18. A method for providing a catheter configured to detect at least one blood gas parameter present in blood in a blood vessel of a patient, the method comprising:
providing a catheter wall forming at least one lumen configured for catherization;
providing at least one optical fiber incorporated on an exterior surface of the catheter wall, wherein the at least one optical fiber comprising at least one blood gas parameter sensor configured to detect the at least one blood gas parameter.

19. The catheter of claim 18, further comprising:
propagating an optical signal through a core of the optical fiber, wherein the optical fiber is fabricated with a series of wells into at least the cladding of the optical fiber, and wherein the wells have been filled with at least one material sensitive to a target blood gas parameter to form sensor wells;
detecting an optical signal which has propagated through the fabricated optical fiber with sensor wells;
processing the detected optical signal to determine blood gas parameters at each of the optical fiber sensor wells.

* * * * *